United States Patent [19]
Sato et al.

[11] Patent Number: 5,554,779
[45] Date of Patent: Sep. 10, 1996

[54] ORGANOSILICON COMPOUND AND A METHOD FOR PREPARING THE SAME

[75] Inventors: Shinichi Sato, Annaka; Noriyuki Koike, Gunma-ken, both of Japan

[73] Assignee: Shin-Etsu Chemical Co., Ltd., Tokyo, Japan

[21] Appl. No.: 558,001

[22] Filed: Nov. 13, 1995

[30] Foreign Application Priority Data

Nov. 11, 1994 [JP] Japan ................... 6-302998

[51] Int. Cl.$^6$ ................... C07F 7/10
[52] U.S. Cl. ................... 556/419
[58] Field of Search ................... 556/419

[56] References Cited

U.S. PATENT DOCUMENTS

| | | | |
|---|---|---|---|
| 5,300,613 | 4/1994 | Kishita et al. | 556/419 X |
| 5,380,811 | 1/1995 | Kishita et al. | 556/419 X |

FOREIGN PATENT DOCUMENTS

| | | |
|---|---|---|
| 0496597 | 7/1992 | European Pat. Off. |
| 0573282 | 12/1993 | European Pat. Off. |
| 0601883 | 6/1994 | European Pat. Off. |

*Primary Examiner*—Paul F. Shaver
*Attorney, Agent, or Firm*—Oblon, Spivak, McClelland, Maier, & Neustadt, P.C.

[57] ABSTRACT

This invention provides an organosilicon compound represented by the following general formula (1):

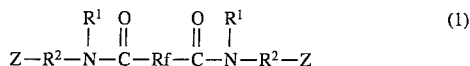

wherein $R^1$ are independently a hydrogen atom or an unsubstituted or substituted monovalent hydrocarbon group such as methyl, phenyl, 3,3,3-trifluoropropyl and 6,6,6,5,5,4,4,3,3-nonafluorohexyl groups, $R^2$ are independently an alkylene group such as ethylene and propylene groups, Rf is a perfluoroalkylene group, such as —$C_4F_8$— and —$C_6F_{12}$—, or a divalent perfluoropolyether group, such as a group having the formula:

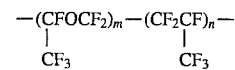

wherein m and n are each an integer such that m+n is 2 to 200, and Z is a group having the general formula:

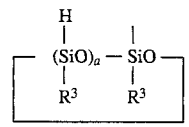

wherein $R^3$ are independently the same unsubstituted or substituted monovalent hydrocarbon group as the group $R^1$, and a is an integer of 2 to 4. This compound is useful as a crosslinking agent which is used when curing an unsaturated group-containing polymer by hydrosilylation reaction.

16 Claims, 3 Drawing Sheets

ORGANOSILICON COMPOUND AND A METHOD FOR PREPARING THE SAME

BACKGROUND OF THE INVENTION

1. Field of the Invention

The present invention relates to an organosilicon compound useful as a crosslinking agent for addition-reaction curable silicone rubber compositions for use in various uses, and to a method for preparing the organosilicon compound.

2. Description of the Prior Art

Conventionally, an addition-reaction curable silicone rubber composition comprising an organopolysiloxane having, as a base polymer, an alkenyl group such as vinyl group and, as a crosslinking agent, an organohydrogenpolysiloxane having a SiH group compounded therewith are utilized in various uses. The curable silicone rubber compositions of this type are cured by the addition reaction (hydrosilylation reaction) between the SiH group of the crosslinking agent and the alkenyl group of the base polymer.

However, in the case of using, as a base polymer, a fluorosilicone or fluoropolymer high in fluorine content, even if a conventional organohydrogenpolysiloxane is used as a crosslinking agent, a good cured product could not be obtained from a silicone rubber composition comprised of a combination of said components since the crosslinking agent is poor in compatibility with the fluorosilicone or fluoropolymer high in fluorine content.

Also, Japanese Patent Pre-examination Publication (kokai) Nos. 62-47605, 62-49305, 62-47608, 4-243884, and 6-159510 describe a fluorine-containing organohydrogenpolysiloxane represented by the following general formula:

$$\begin{array}{cc} \text{Me} & \text{Me} \\ | & | \\ (\text{HSiO})_3\text{SiCH}_2\text{CH}_2-\text{Rf}-\text{CH}_2\text{CH}_2\text{Si}(\text{OSiH})_3 \\ | & | \\ \text{Me} & \text{Me} \end{array}$$

wherein Rf is a divalent perfluoroalkylene group or a divalent perfluoropolyether group, and Me stands for a methyl group, or a fluorine-containing organohydrogenpolysiloxane represented by the following general formula:

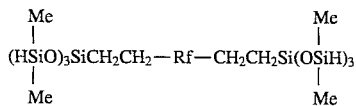

wherein Rf' is a monovalent perfluoroalkyl group or a monovalent perfluoropolyether group, and Me has the same meaning as above.

However, there has not hitherto been reported a compound in which two cyclic organohydrogensiloxanes are linked to each other through a divalent perfluoroalkylene group or a divalent perfluoropolyether group.

SUMMARY OF THE INVENTION

Accordingly, an object of the present invention is to provide an organosilicon compound which has an improved compatibility with a fluorosilicone or fluoropolymer having a high fluorine-content and is useful as a crosslinking agent for addition-reaction curable silicone rubber compositions or addition-reaction curable fluororubber compositions each high in fluorine content, and a method for preparing the organosilicon compound.

This invention provides an organosilicon compound represented by the following general formula (1):

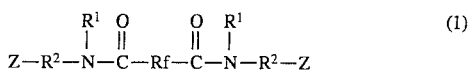

wherein $R^1$ are independently a hydrogen atom or an unsubstituted or substituted monovalent hydrocarbon group, $R^2$ are independently an alkylene group, Rf is a perfluoroalkylene group or a divalent perfluoropolyether group, and Z is a group having the general formula:

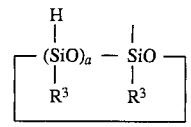

wherein $R^3$ are independently an unsubstituted or substituted monovalent hydrocarbon group, and a is an integer of 2 to 4.

This invention provides also a method for preparing the organosilicon compound represented by said general formula (1), comprising subjecting an excess amount of a cyclic organohydrogenpolysiloxane represented by the following general formula (2):

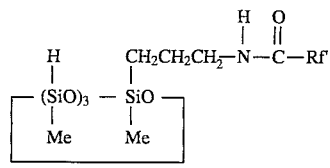

wherein $R^3$ and a are as defined above, and a fluorine-containing amide compound having an unsaturated group represented by the following general formula (3):

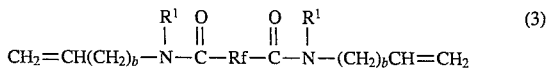

wherein Rf and $R^1$ are as defined above, b are independently an integer of 0 to 4, and preferably 0 or 1, to partial addition reaction in the presence of a catalyst.

The organosilicon compound of the present invention is useful as a crosslinking agent for addition-reaction curable silicone compositions. Particularly, this compound is useful as a crosslinking agent for addition-reaction curable fluorosilicone compositions and addition-reaction curable fluororubber compositions each high in fluorine content.

DETAILED DESCRIPTION OF THE PREFERRED EMBODIMENTS

Figure 1:
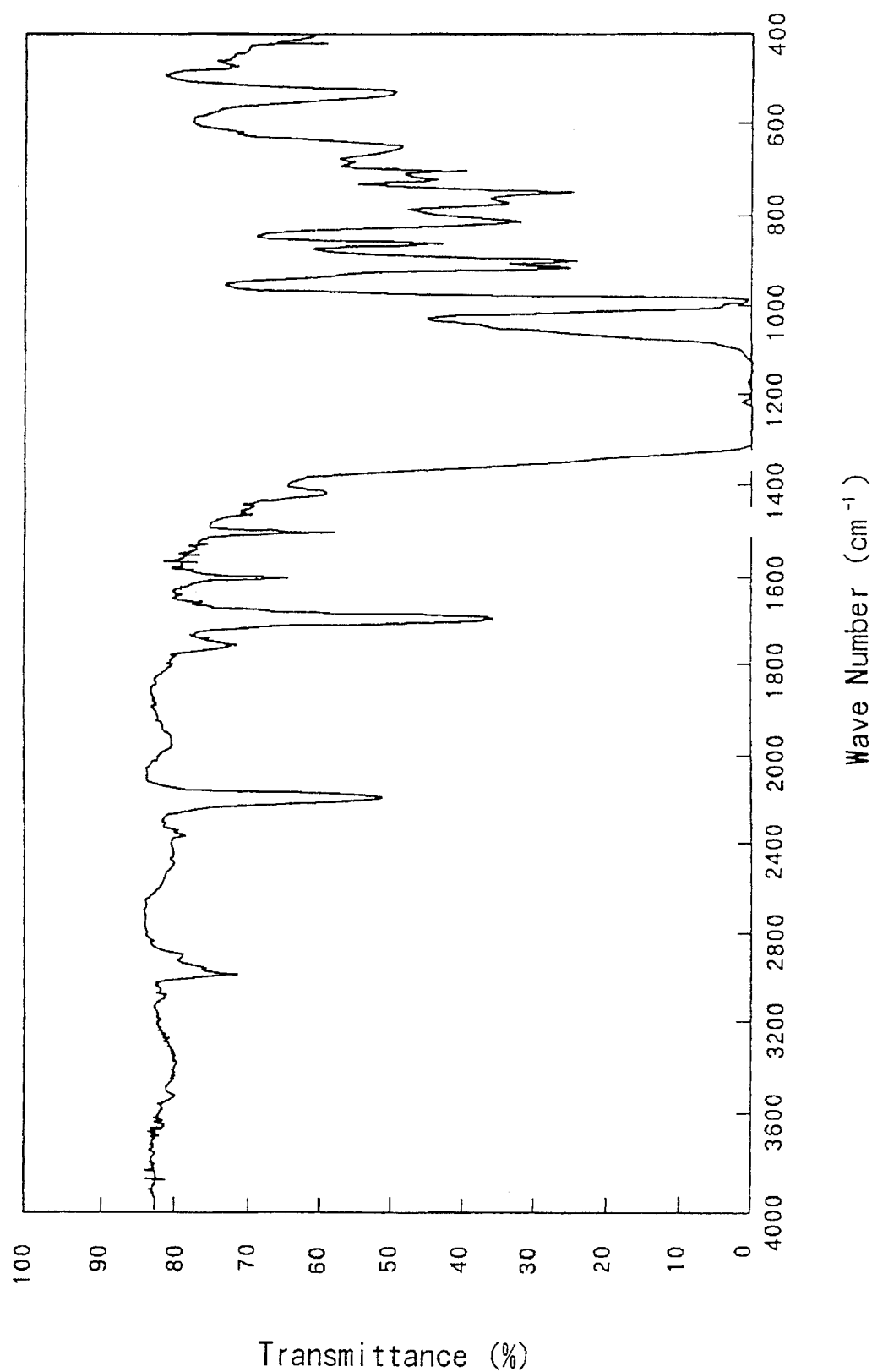
FIG. 1 is an IR chart of the organosilicon compound of the present invention obtained. in Example 1.

The present invention is hereinafter described in more detail.

Organosilicon compounds

The organosilicon compound of the present invention is represented by the above general formula (1). In this formula, the unsubstituted or substituted monovalent hydrocarbon group of $R^1$ is exemplified by an unsubstituted or substituted monovalent hydrocarbon group having 1 to 12 carbon atoms, for example, alkyl groups such as methyl, ethyl, propyl, isopropyl, butyl, isobutyl, tert-butyl, pentyl, neopentyl, hexyl, heptyl, octyl, nonyl, decyl, and dodecyl groups; cycloalkyl groups such as cyclopentyl, cyclohexyl, and cycloheptyl groups; alkenyl groups such as vinyl, allyl, propenyl, isopropenyl, butenyl, isobutenyl, hexenyl, and cyclohexenyl groups; aryl groups such as phenyl, tolyl, xylyl, naphthyl, and biphenyl groups; aralkyl groups such as benzyl, phenylethyl, phenylpropyl, and methylbenzyl groups; and groups derived from said exemplified groups by substituting at least part of the hydrogens bonded to the carbon atoms thereof with, for example, halogen atoms such as fluorine, chlorine and bromine, or cyano groups, such as chloromethyl, 2-bromoethyl, 3-chloropropyl, 3,3,3-trifluoropropyl, chlorophenyl, fluorophenyl, cyanoethyl, and 6,6,6,5,5,4,4,3,3-nonafluorohexyl groups, and preferably an unsubstituted or substituted monovalent hydrocarbon group free of aliphatic unsaturation having 1 to 8 carbon atoms, and more preferably methyl, phenyl, 3,3,3-trifluoropropyl, and 6,6,6,5,5,4,4,3,3-nonafluorohexyl groups.

In the above general formula (1), the divalent alkylene group of $R^2$ includes, for example, an alkylene group having 1 to 6 carbon atoms, such as methylene, ethylene, propylene, tetramethylene, hexamethylene, and methylpropylene, and preferably a straight chain or branched alkylene group having 2 to 4 carbon atoms, and more preferably ethylene and propylene groups.

In the above general formula (1), the perfluoroalkylene group of Rf includes, for example, a perfluoroalkylene group having 2 to 10 carbon atoms, such as $-C_2F_4-$, $-C_3F_6-$, $-C_4F_8-$, $-C_6F_{12}-$ and $-C_8F_{16}-$, and preferably a straight chain perfluoroalkylene group having 2 to 8 carbon atoms, and more preferably $-C_4F_8-$ and $-C_6F_{12}-$.

In the above general formula (1), the divalent perfluoropolyether group of Rf includes, for example, a straight chain or branched divalent perfluoropolyether group having 6 to 600 carbon atoms in which one or more repeating units such as $-CF_2O-$, $-CF_2CF_2O-$, $-CF_2CF_2CF_2O-$ and $-CF(CF_3)OCF_2-$ are contained, such as a perfluoropolyether group represented by the following formula:

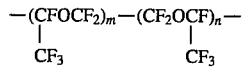

wherein m and n are each an integer so that m+n is 2 to 200, preferably 3 to 60, and more preferably 4 to 40; a perfluoropolyether group represented by the following formula:

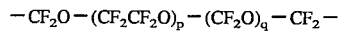

wherein p is an integer of 5 to 100, and q is an integer of 1 to 30; and a perfluoropolyether group represented by the following formula:

wherein r is an integer of 4 to 100; and preferably a straight chain or branched divalent perfluoropolyether group having 9 to 200 carbon atoms, and more preferably said perfluoropolyether group represented by the formula:

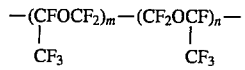

wherein m and n are as defined above.

In the above general formula (1), the unsubstituted or substituted monovalent hydrocarbon group of $R^3$ in the group Z represented by the following formula:

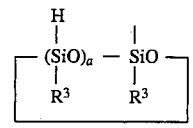

includes, for example, the same unsubstituted or substituted monovalent hydrocarbon group as those represented by $R^1$ of the above general formula (1), generally an unsubstituted or substituted monovalent hydrocarbon group having 1 to 12 carbon atoms, preferably an unsubstituted or substituted monovalent hydrocarbon group free of aliphatic unsaturation and having 1 to 12 carbon atoms, and more preferably methyl, phenyl, 3,3,3-trifluoropropyl, and 6,6,6,5,5,4,4,3,3-nonafluorohexyl groups. The a in the above group Z is an integer of 2, 3 or 4.

Method for preparing the organosilicon compound

The compound of the present invention can be synthesized, for example, by subjecting an excess amount of a cyclic organohydrogenpolysiloxane represented by the following general formula (2):

wherein $R^3$ and a are as defined above, and a fluorine-containing amide compound having an unsaturated group represented by the following general formula (3):

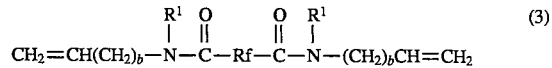

wherein Rf and $R^1$ are as defined above, b are independently an integer of 0 to 4, and preferably 0 or 1, to partial addition reaction in the presence of a catalyst.

The above catalyst includes, for example, the Group VIII elements of the periodic table and their compounds, such as, chloroplatinic acid; an alcohol-modified chloroplatinic acid (see U.S. Pat. No. 3,220,972); a complex of chloroplatinic acid with an olefin (see U.S. Pat. Nos. 3,159,601; 3,159,662; and 3,775,452); a platinum black, palladium or the like supported on a carrier such as alumina, silica or carbon; a rhodium-olefin complex; and chlorotris(triphenylphosphine)rhodium [Wilkinson's catalyst].

These complexes are preferably dissolved in an organic solvent such as alcohols, ketones or ethers for use.

The reaction temperature is preferably 50° to 150° C., and more preferably 60° to 120° C.

The amount of said catalyst used may be a so-called catalytic amount, for example, 1 to 1,000 ppm, preferably 10 to 500 ppm, in terms of a platinum family metal, based on the cyclic organohydrogenpolysiloxane.

The thus obtained organosilicon compound is useful as a crosslinking agent for addition-reaction curable silicone rubber compositions.

The addition-reaction curable silicone rubber compositions in which the organosilicon compound of the present invention is present as a crosslinking agent can be obtained, for example, by mixing an organopolysiloxane base polymer having an alkenyl group with the organosilicon compound in such an amount that the content of the SiH groups in said compound is 0.5 to 5 mol, preferably 0.8 to 3 mol, per mol of said alkenyl group and further mixing therewith a curing catalyst, a filler, and the like. The obtained addition-reaction curable silicone rubber compositions can be used for various uses, and particularly, a cured product obtained by curing a composition comprising an organopolysiloxane base polymer into which a fluorine-containing group has been introduced is excellent in adhesion to substrates.

EXAMPLES

The present invention will be hereinafter described in more detail.

Example 1

Into a four-necked 1-liter flask equipped with a stirrer, a thermometer, a reflux condenser and a dropping funnel, 152.1 g of 1,3,5,7-tetramethylcyclotetrasiloxane, 0.5 g of a toluene solution in which a complex of chloroplatinic acid with 1,3-divinyl-1,1,3,3-tetramethyldisiloxane has been dissolved in an amount of 0.5 weight % in terms of platinum atom, and 150 g of metaxylene hexafluoride were charged and heated to 80° C. Then, into this flask, a solution prepared by dissolving, in 150 g of metaxylene hexafluoride, 140.8 g of a fluorinecontaining allylamide represented by the following structural formula:

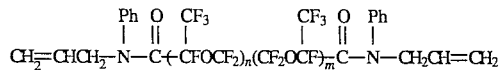

wherein Ph stands for a phenyl group, and m and n are each an integer of 5 to 27, provided that m+n equals to 32 on average, was dropwise added over 1 hour. The resulting mixture solution was further reacted at 80° C. for 1 hour, followed by distilling off the 1,3,5,7-tetramethylcyclotetrasiloxane and metaxylene hexafluoride from the reaction mixture under reduced pressure. Then, the resulting liquid was extracted three times with hexane, followed by distilling off the hexane from the thus obtained extract under reduced pressure to produce 150.1 g (yield: 98.2 %) of a liquid having a refractive index of 1.3293 at 25° C. From the results of $^1$H-NMR, IR and elemental analyses for this liquid, it was confirmed that the liquid is a compound having the following structure. The results of the $^1$H-NMR, IR and elemental analyses are shown in the following, and the IR chart is shown in FIG. 1.

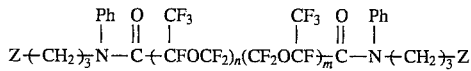

wherein Z is a group represented by the following formula:

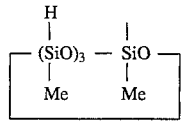

wherein Me stands for a methyl group, Ph stands for a phenyl group, and m and n are each an integer of 5 to 27, provided that m+n equals to 32 on average. $^1$H-NMR (Standard: TMS)

δ 0.01 ppm (s, Si—CH$_3$, 24H)
δ 0.41 ppm (m, Si—CH$_2$, 4H)
δ 1.53 ppm (m, C—CH$_2$—C, 4H)
δ 3.52 ppm (t, N—CH$_2$, 4H)
δ 4.49 ppm (s, Si-H, 6H)
δ 6.8–7.3 ppm (m, arom., 10H)

IR
$^\nu$Si—H: 2170 cm$^{-1}$
$^\nu$C=O: 1695 cm$^{-1}$
Elemental analysis

|  | C | H | O | Si |
|---|---|---|---|---|
| Found | 24.06% | 0.86% | 11.03% | 3.69% |
| Calc'd | 24.18% | 0.79% | 11.10% | 3.72% |

Example 2

Figure 2:
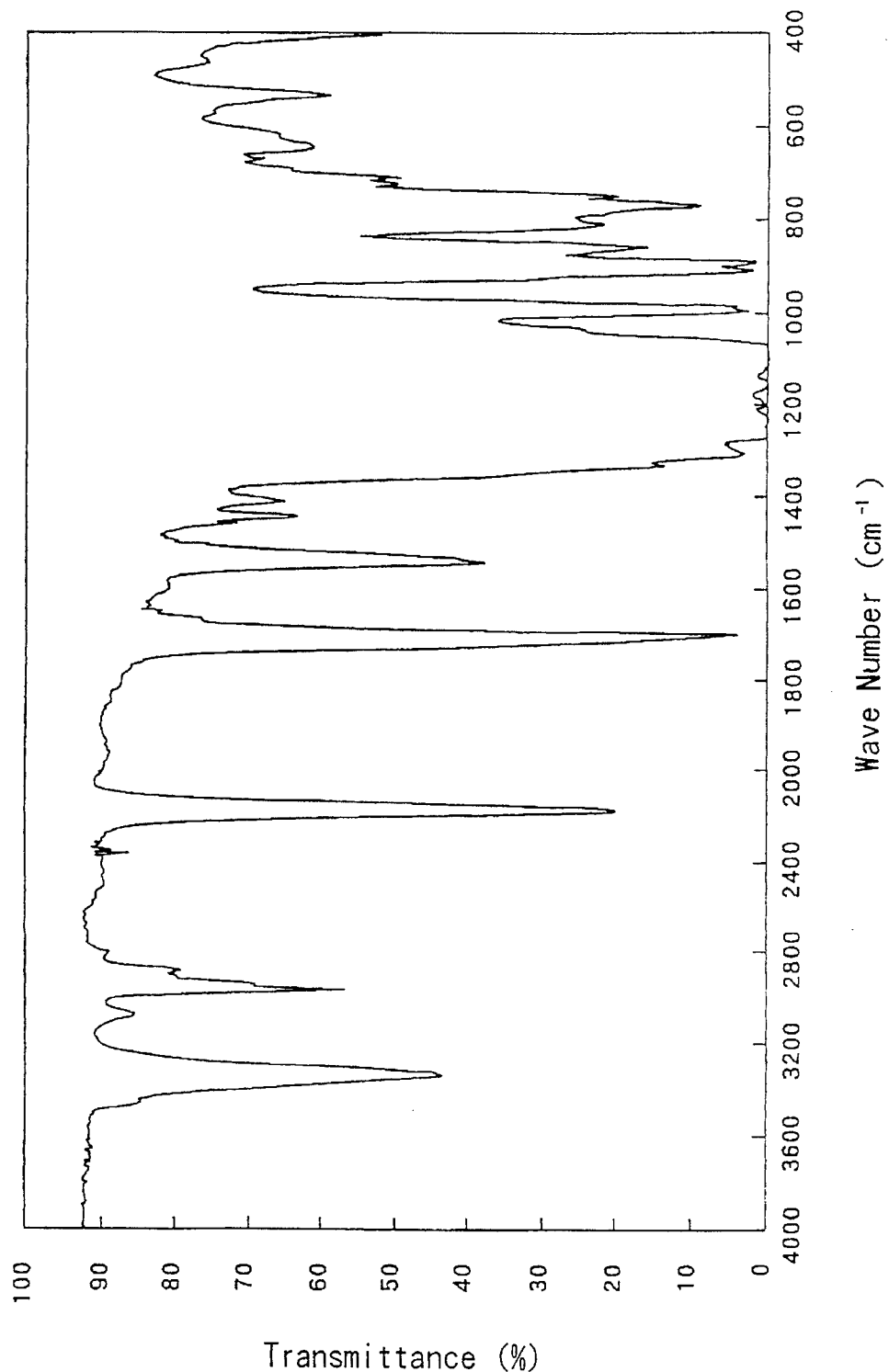
FIG. 2 is an IR chart of the organosilicon compound of the present invention obtained in Example 2.

Into a four-necked 1-liter flask equipped with a stirrer, a thermometer, a reflux condenser and a dropping funnel, 125.1 g of 1,3,5,7,9-pentamethylcyclopentasiloxane, 0.1 g of a toluene solution in which a complex of chloroplatinic acid with 1,3-divinyl-1,1,3,3-tetramethyldisiloxane has been dissolved in an amount of 0.5 weight % in terms of platinum atom, and 120 g of metaxylene hexafluoride were charged and heated to 80° C. Then, into this flask, a solution prepared by dissolving, in 20 g of metaxylene hexafluoride, 20.0 g of a fluorine-containing allylamide represented by the following structural formula:

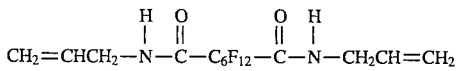

was dropwise added over 1 hour. The resulting mixture solution was further reacted at 80° C. for 1 hour, followed by distilling off the 1,3,5,7,9-pentamethylcyclopentasiloxane and metaxylene hexafluoride from the reaction mixture under reduced pressure. Then, the resulting liquid was extracted three times with hexane, followed by distilling off the hexane from the thus obtained extract under reduced pressure to produce 40.1 g (yield: 87.9 %) of a liquid having a refractive index of 1.3865 at 25° C. From the results of $^1$H-NMR, IR and elemental analyses for this liquid, it was confirmed that the liquid is a compound having the following structure. The results of the $^1$H-NMR, IR and elemental analyses are shown in the following, and the IR chart is shown in FIG. 2.

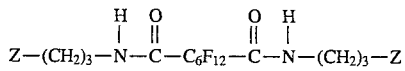

wherein Z is a group represented by the following formula:

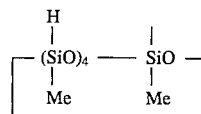

wherein Me stands for a methyl group.
$^1$H-NMR (Standard: TMS)
δ 0.04 ppm (s, Si—CH$_3$, 30H)
δ 0.47 ppm (m, Si—CH$_2$, 4H)
δ 1.51 ppm (m, C—CH$_2$—C, 4H)
δ 3.17 ppm (t, N—CH$_2$, 4H)
δ 4.53 ppm (s, Si—H, 8H)
δ 6.74 ppm (s, N—H, 2H)

IR
$^\nu$N—H: 3330 cm$^{-1}$
$^\nu$Si—H: 2170 cm$^{-1}$
$^\nu$C=O: 1700 cm$^{-1}$
Elemental analysis

|  | C | H | O | Si |
|---|---|---|---|---|
| Found | 29.47% | 4.94% | 16.25% | 22.88% |
| Calc'd | 29.50% | 4.95% | 16.37% | 22.99% |

Example 3

Figure 3:
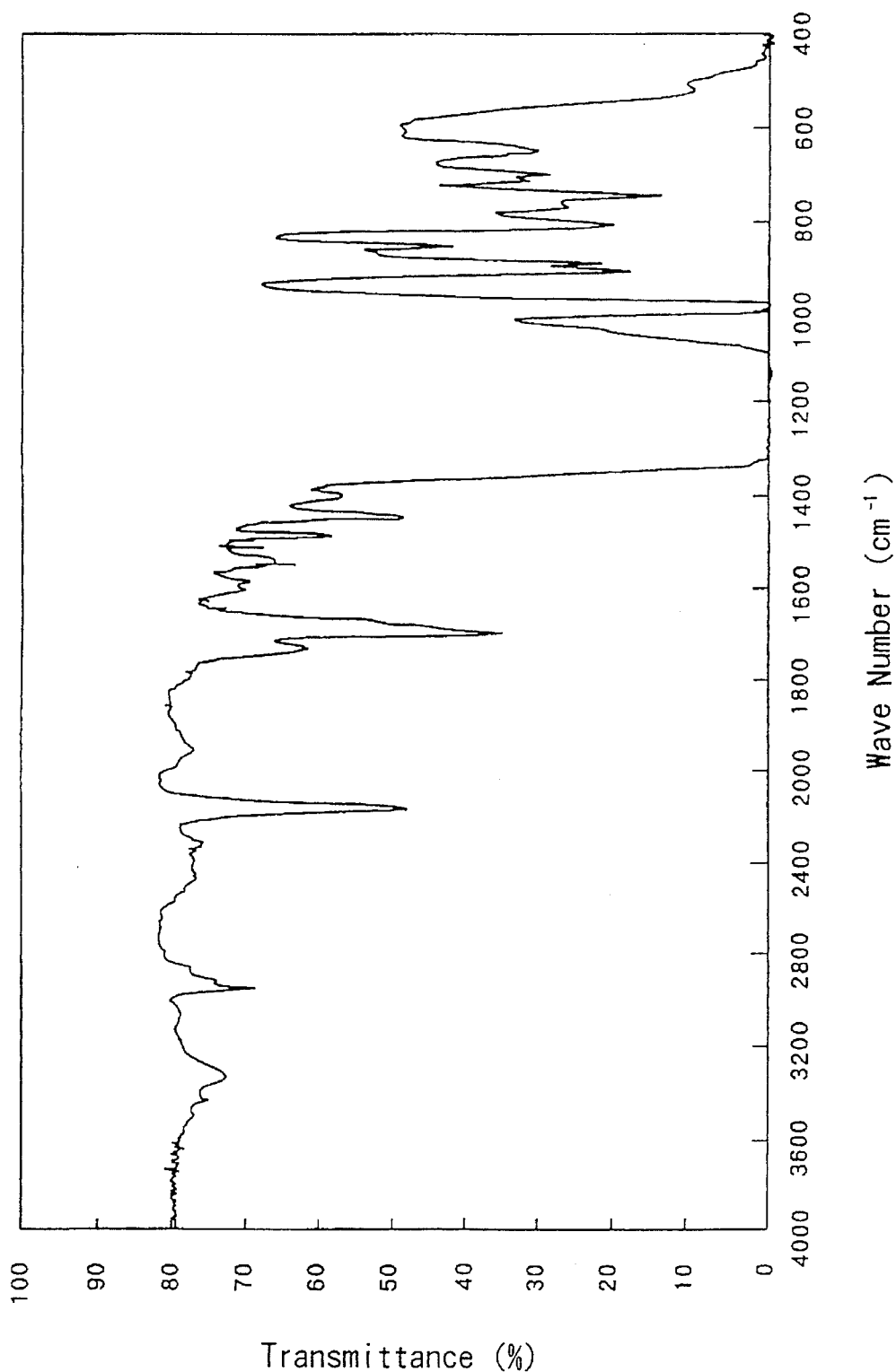
FIG. 3 is an IR chart of the organosilicon compound of the present invention obtained in Example 3.

Into a four-necked 1-liter flask equipped with a stirrer, a thermometer, a reflux condenser and a dropping funnel, 28.0 g of 1,3,5,7-tetramethylcyclotetrasiloxane, 0.05 g of a toluene solution in which a complex of chloroplatinic acid with 1,3-divinyl-1,1,3,3-tetramethyldisiloxane has been dissolved in an amount of 0.5 weight % in terms of platinum atom, and 20 g of metaxylene hexafluoride were charged and heated to 80° C. Then, into this flask, a solution prepared by dissolving, in 20 g of metaxylene hexafluoride, 20.0 g of a fluorine-containing allylamide represented by the following structural formula:

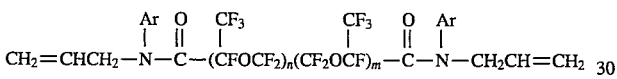

wherein Ar stands for a group represented by the following formula:

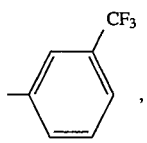

and m and n are each an integer of 5 to 27, provided that m+n equals to 32 on average, was dropwise added over 1 hour. The resulting mixture solution was further reacted at 80° C. for 1 hour, followed by distilling off the 1,3,5,7-tetramethylcyclotetrasiloxane and metaxylene hexafluoride from the reaction mixture under reduced pressure. Then, the resulting liquid was extracted three times with hexane, followed by distilling off the hexane from the thus obtained extract under reduced pressure to produce 15.2 g (yield: 70.1%) of a liquid having a refractive index of 1.3278 at 25° C. From the results of $^1$H-NMR, IR and elemental analyses for this liquid, it was confirmed that the liquid is a compound having the following structure. The results of the $^1$H-NMR, IR and elemental analyses are shown in the following, and the IR chart is shown in FIG. 3.

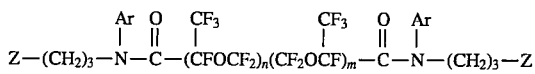

wherein Z is a group represented by the following formula:

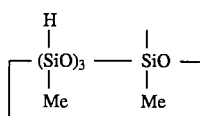

wherein Me stands for a methyl group, Ar stands for a group represented by the following formula:

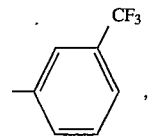

and m and n are each an integer of 5 to 27, provided that m+n equals to 32 on average.
$^1$H-NMR (Standard: TMS).

δ 0.01 ppm (s, Si—CH$_3$, 24H)
δ 0.41 ppm (m, Si—CH$_2$, 4H)
δ 1.54 ppm (m, C—CH$_2$—C, 4H)
δ 3.54 ppm (t, N—CH$_2$, 4H)
δ 4.41 ppm (s, Si—H, 6H)
δ 7.1–7.6 ppm (m, arom., 8H)

IR
$^\nu$Si—H: 2170 cm$^{-1}$
$^\nu$C=O: 1700 cm$^{-1}$
Elemental analysis

|  | C | H | O | Si |
|---|---|---|---|---|
| Found | 24.25% | 0.79% | 10.70% | 3.62% |
| Calc'd | 24.21% | 0.81% | 10.75% | 3.59% |

What is claimed is:

1. An organosilicon compound represented by the following general formula (1):

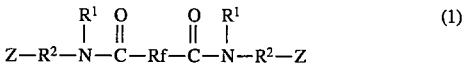 (1)

wherein R$^1$ are independently a hydrogen atom or an unsubstituted or substituted monovalent hydrocarbon group, R$^2$ are independently an alkylene group, Rf is a perfluoroalkylene group or a divalent perfluoropolyether group, and Z is a group having the general formula:

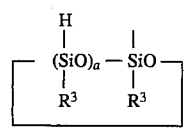

wherein R$^3$ are independently an unsubstituted or substituted monovalent hydrocarbon group, and a is an integer of 2 to 4.

2. The organosilicon compound according to claim 1, wherein the R$^1$ in said general formula (1) are an unsubstituted or substituted monovalent hydrocarbon group free of aliphatic unsaturation having 1 to 12 carbon atoms.

3. The organosilicon compound according to claim 1, wherein the R$^1$ in said general formula (1) are selected from the group consisting of methyl, phenyl, 3,3,3-trifluoropropyl, and 6,6,6,5,5,4,4,3,3-nonafluorohexyl groups.

4. The organosilicon compound according to claim 1, wherein the R$^2$ in said general formula (1) are a straight chain or branched alkylene group having 1 to 6 carbon atoms.

5. The organosilicon compound according to claim 1, wherein the R$^2$ in said general formula (1) are selected from the group consisting of ethylene and propylene groups.

6. The organosilicon compound according to claim 1, wherein the perfluoroalkylene group among the Rf in said general formula (1) is a straight chain perfluoroalkylene group having 2 to 10 carbon atoms, and the divalent perfluoropolyether group among the Rf in said general formula (1) is a straight chain or branched divalent perfluoropolyether group having 6 to 600 carbon atoms in which one or more repeating units selected from the group consisting of $-CF_2O-$, $-CF_2CF_2O-$, $-CF_2CF_2CF_2O-$, and $-CF(CF_3)OCF_2-$ are contained.

7. The organosilicon compound according to claim 1, wherein the perfluoroalkylene group among the Rf in said general formula (1) are selected from the group consisting of $-C_2F_4-$, $-C_3F_6-$, $-C_4F_8-$, $-C_6F_{12}-$, and $-C_8F_{16}-$, and the divalent perfluoropolyether group among the Rf in said general formula (1) is a group represented by the formula:

$$-(CFOCF_2)_m-(CF_2OCF)_n- \atop \phantom{-(}CF_3 \phantom{)_m-(CF_2OCF)_n}CF_3$$

wherein m and n are each an integer such that m+n is 2 to 200.

8. The organosilicon compound according to claim 1, wherein the $R^3$ in the group Z of said general formula (1) are an unsubstituted or substituted monovalent hydrocarbon group free of aliphatic unsaturation having 1 to 12 carbon atoms.

9. The organosilicon compound according to claim 1, wherein the $R^3$ in the group Z of said general formula (1) are selected from the group consisting of methyl, phenyl, 3,3,3-trifluoropropyl, and 6,6,6,5,5,4,4,3,3-nonafluorohexyl groups.

10. The organosilicon compound according to claim 1, represented by the general formula:

$$Z-(CH_2)_3-\underset{\underset{H}{|}}{N}-\underset{\underset{}{\overset{O}{\|}}}{C}-(CFOCF_2)_n(CF_2OCF)_m-\underset{\underset{}{\overset{O}{\|}}}{C}-\underset{\underset{H}{|}}{N}-(CH_2)_3-Z$$

(with Ph and CF_3 substituents)

wherein Z is a group represented by the formula:

$$\left[-(SiO)_3 \underset{Me}{\overset{H}{|}} - SiO- \underset{Me}{|}\right]$$

wherein Me stands for a methyl group, Ph stands for a phenyl group, and m and n are each an integer of 5 to 27, provided that m+n equals 32 on average.

11. The organosilicon compound according to claim 1, represented by the general formula:

$$Z-(CH_2)_3-\underset{\underset{H}{|}}{N}-\underset{\overset{O}{\|}}{C}-C_6F_{12}-\underset{\overset{O}{\|}}{C}-\underset{\underset{H}{|}}{N}-(CH_2)_3-Z$$

wherein Z is a group represented by the formula:

$$\left[-(SiO)_4 \underset{Me}{\overset{H}{|}} - SiO- \underset{Me}{|}\right]$$

wherein Me stands for a methyl group.

12. The organosilicon compound according to claim 1, represented by the general formula:

$$Z-(CH_2)_3-\underset{\underset{H}{|}}{N}-\underset{\overset{O}{\|}}{C}-(CFOCF_2)_n(CF_2OCF)_m-\underset{\overset{O}{\|}}{C}-\underset{\underset{H}{|}}{N}-(CH_2)_3-Z$$

(with Ar and CF_3 substituents)

wherein Z is a group represented by the formula:

$$\left[-(SiO)_3 \underset{Me}{\overset{H}{|}} - SiO- \underset{Me}{|}\right]$$

wherein Me stands for a methyl group, Ar stands for a group represented by the formula:
and m and n are each an integer of 5 to 27, provided that m+n equals to 32 on average.

13. A method for preparing the organosilicon compound of claim 1, which comprises subjecting an excess amount of a cyclic organohydrogenpolysiloxane represented by the following general formula (2):

$$\left[-(SiO)_{a+1} \underset{R^3}{\overset{H}{|}} -\right] \quad (2)$$

wherein $R^3$ are represents an unsubstituted or substituted monovalent hydrocarbon group, and a is an integer of 2 to 4, and a fluorine-containing amide; compound having an unsaturated group represented by the following general formula (3):

$$CH_2=CH(CH_2)_b-\underset{\underset{R^1}{|}}{N}-\underset{\overset{O}{\|}}{C}-Rf-\underset{\overset{O}{\|}}{C}-\underset{\underset{R^1}{|}}{N}-(CH_2)_bCH=CH_2 \quad (3)$$

wherein $R_1$ are independently a hydrogen atom or an unsubstituted or substituted monovalent hydrocarbon group, Rf is a perfluoroalkylene group or a divalent perfluoropolyether group, and b are independently an integer of 0 to 4, to partial addition reaction in the presence of a catalyst.

14. The method according to claim 13, wherein the catalyst comprises the Group VIII elements of the periodic table or their compounds.

15. The method according to claim 13, wherein the amount of the catalyst is in the range of 1 to 1,000 ppm, in terms of a platinum family metal, based on the cyclic organohydrogenpolysiloxane.

16. The method according to claim 13, wherein the reaction temperature is in the range of 50° to 150° C.

* * * * *